United States Patent
Hoehne et al.

(10) Patent No.: US 9,062,905 B2
(45) Date of Patent: Jun. 23, 2015

(54) LOW TEMPERATURE DEVICE WITH LOW-VIBRATION SAMPLE HOLDING DEVICE

(75) Inventors: Jens Hoehne, Munich (DE); Matthias Buehler, Poecking (DE)

(73) Assignee: HB Patent Unternehmergesellschaft, Munich (DE)

( * ) Notice: Subject to any disclaimer, the term of this patent is extended or adjusted under 35 U.S.C. 154(b) by 1073 days.

(21) Appl. No.: 12/653,059

(22) Filed: Dec. 7, 2009

(65) Prior Publication Data

US 2010/0089069 A1    Apr. 15, 2010

Related U.S. Application Data

(63) Continuation of application No. PCT/EP2008/057055, filed on Jun. 6, 2008.

(30) Foreign Application Priority Data

Jun. 22, 2007    (DE) .......................... 10 2007 028 865

(51) Int. Cl.
  *F25D 19/00*    (2006.01)
  *F17C 3/08*    (2006.01)
  (Continued)

(52) U.S. Cl.
  CPC ................ *F25D 19/00* (2013.01); *F17C 3/085* (2013.01); *H01J 37/20* (2013.01); *G01Q 30/10* (2013.01);
  (Continued)

(58) Field of Classification Search
  USPC ....................................... 62/51.1, 6; 3/51.1, 6
  See application file for complete search history.

(56) References Cited

U.S. PATENT DOCUMENTS 4,161,747 A * 7/1979 Frosh et al. .................... 257/716
4,920,803 A * 5/1990 Karaki et al. .................... 73/606
(Continued)

FOREIGN PATENT DOCUMENTS

DE    10056131 A1    11/1999
EP    0585001 A2    8/1992
(Continued)

OTHER PUBLICATIONS

G. Meyer, "A Simple Low-Temperature Ultrahigh-Vacuum Scanning Tunneling Microscope Capable of Atomic Manipulation," review of Scientific Instruments, AIP, Melville, NY, Bd 67, Nr 8, Aug. 1, 1996; pp. 2960-2965 XP000620468 ISSN: 0034-6748.

*Primary Examiner* — John F Pettitt
(74) *Attorney, Agent, or Firm* — Imperium Patent Works; Darien K. Wallace

(57) ABSTRACT

A low temperature device has a low temperature container with an investigational opening. A material sample to that is to be examiner is mounted on a sample-holding device in the low temperature container. A sample that is fastened to the sample holding device can be cooled to the desired temperature using a cooling device, such as a pulse tube cooler, with a cold head that is inside the low temperature container. The sample holder is disposed in the low temperature container in such a way that the sample can be seen through the investigational opening. Because the investigational opening is flexible and not rigidly connected to the low temperature container, vibrations produced by the mechanical cooling device are prevented from being transferred to the investigational opening. Thus, a vibration-sensitive investigating and manipulating device can be coupled to the investigational opening without vibrations being transferred to the investigating and manipulating device.

23 Claims, 2 Drawing Sheets

(51) Int. Cl.
*H01J 37/20* (2006.01)
*G01Q 30/10* (2010.01)
*G01Q 70/02* (2010.01)
*G01Q 70/04* (2010.01)
*G03F 7/20* (2006.01)
*G01N 21/01* (2006.01)

(52) U.S. Cl.
CPC ............... *G01Q 70/02* (2013.01); *G01Q 70/04* (2013.01); *H01J 2237/2001* (2013.01); *G01N 21/01* (2013.01); *G03F 7/70808* (2013.01); *F25B 2500/13* (2013.01)

(56) References Cited

U.S. PATENT DOCUMENTS

| | | | |
|---|---|---|---|
| 4,954,713 A | 9/1990 | Le Bris et al. | 250/458.1 |
| 5,018,359 A * | 5/1991 | Horikawa et al. | 62/51.1 |
| 5,352,898 A | 10/1994 | Mehta | 250/443.1 |
| 5,533,083 A * | 7/1996 | Nagai et al. | 378/44 |
| 5,611,207 A | 3/1997 | Hess | 62/51.1 |
| 2004/0001200 A1* | 1/2004 | Hirakawa et al. | 356/244 |
| 2005/0126187 A1* | 6/2005 | Li et al. | 62/6 |
| 2008/0098752 A1* | 5/2008 | Hohne | 62/51.1 |
| 2010/0050661 A1* | 3/2010 | Snow et al. | 62/51.1 |

FOREIGN PATENT DOCUMENTS

| | | |
|---|---|---|
| EP | 1406107 A2 | 9/2002 |
| GB | 2322969 A | 3/1997 |
| GB | 2325045 A | 5/1997 |
| JP | 08166331 A | 12/1994 |

\* cited by examiner

LOW TEMPERATURE DEVICE WITH LOW-VIBRATION SAMPLE HOLDING DEVICE

CROSS REFERENCE TO RELATED APPLICATION

This application is filed under 35 U.S.C. §111(a) and is based on and hereby claims priority under 35 U.S.C. §120 and §365(c) from International Application No. PCT/EP2008/057055, filed on Jun. 6, 2008, and published as WO 2009/000629 A2 on Dec. 31, 2008, which in turn claims priority from German Application No. 102007028865.6, filed on Jun. 22, 2007, in Germany. This application is a continuation of International Application No. PCT/EP2008/057055, which is a continuation of German Application No. 102007028865.6. International Application No. PCT/EP2008/057055 is pending as of the filing date of this application, and the United States is an elected state in International Application No. PCT/EP2008/057055. This application claims the benefit under 35 U.S.C. §119 from German Application No. 102007028865.6. The disclosure of each of the foregoing documents is incorporated herein by reference.

TECHNICAL FIELD

The present invention relates to a low temperature device in which a test opening is flexibly connected to a low temperature container.

BACKGROUND

Low temperature devices are used in cryophysics and in sensors that are based on a low temperature effect. Such low temperature devices are disclosed, for example, in European Patent No. EP1014056 A2. Conventional low temperature devices have a low temperature container with at least one test opening. A probe holder is disposed in the low temperature container, and a material probe that is to be investigated is attached to the probe holder. A probe attached to the probe holder can be cooled to the desired temperature using a cooling device with a cooling head placed in the low temperature container. The probe holder and attached probe are so situated in the low temperature container that the probe is visible through the testing opening. A two-stage pulsed tube cooler and a demagnetization stage are used as the cooling device. Instead of a demagnetization stage, a 3He/4He demixing cooler or a 3He cooler can also be used. The pulsed tube cooler pre-cools the probe to about 4 K, and the second cooling device cools to the operating temperature of the sensors based on a low temperature effect to a range of 50-400 mK. Such conventional cryodetector devices are costly because they require two cooling stages and operate at the extremely low operating temperatures of the sensors. Due to these low operating temperatures, multiple infrared filters are needed, as well as many shields in the area of the measuring blowpipe. Consequently, the measuring blowpipe must have a large diameter. A similar conventional low temperature device is also disclosed in German Patent No. DE10317888 B3.

With such low temperature devices it is often necessary for vibration-sensitive investigation and manipulation devices to be coupled to the test opening. For example, this is done by flange-mounting the particular test device onto the test opening. Owing to this mechanical connection, vibrations of the cooling device are transferred to the test device, which is undesirable in some test devices such as optical measuring sections. Such a conventional cooling device is disclosed in U.S. Pat. No. 4,954,713.

Japanese Patent No. JP8166331 discloses a device for characterizing semiconductor probes with a low temperature device that includes a low temperature container with a test opening, a probe holder that is situated in the low temperature container, and a cooling device that is thermally coupled to the probe holder. German Patent No. DE10056131 discloses a cooling device that includes a low temperature container, a probe holder that is situated in the low temperature container, and a cooling device that is thermally coupled to the probe holder. Additional related cooling devices are disclosed in European Patent Nos. EP0585001 and EP1406107 and United Kingdom Patent Nos. GB2325045 and GB2322969.

A low temperature device is sought that allows vibration-sensitive test and manipulation devices to be directly connected to a test window.

SUMMARY

The invention discloses a low temperature device that has a low temperature container with at least one investigational or test opening. A sample-holding device on which a material sample to be examined can be mounted is disposed in the low temperature container. A sample, fastened to the sample holding device, can be cooled to the desired temperature by means of a cooling device with a cold head that is disposed in the low temperature container. The sample holder, or the sample disposed thereon, is disposed in the low temperature container in such a way that the sample can be seen through the test opening. A pulse tube cooler is used as a cooling device. For such low temperature devices, it is frequently necessary to couple the vibration-sensitive investigating and manipulating devices to the test opening. Because the test opening is flexible and not rigidly connected to the low temperature container, vibrations produced by the mechanical cooling device are prevented from being transferred to the test opening. At the least, extensive damping occurs. With that, a vibration-sensitive investigating and manipulating device can be coupled directly to the test opening, for example, by flanging, without vibrations being transferred to the investigating and manipulating device.

By having the test opening be flexibly, as opposed to rigidly, connected to the low temperature container, vibrations generated by the mechanical cooling device are prevented from being transferred to the test opening. At a minimum, the vibrations are severely dampened. Thus, a vibration-sensitive test and manipulation device can be connected directly to the test opening, for example flange-connected, without vibrations being transferred to the test and manipulation device.

Thus, vibrations generated by the cooling device are prevented from being transferred to the probe holder and to a probe attached thereon. The probe to be investigated is coupled rigidly and in a nearly vibration-free fashion to the test and manipulation device. The probe placed on the probe holder can therefore be tested without disturbing vibrations. The configuration ensures that radiation can be directed from outside the low temperature container onto the probe, and radiation emitted from the probe can get through the test window into the testing and manipulation device. Extreme mechanical oscillations or vibrations can be prevented from influencing and disturbing the measurement by the test and manipulation device and from affecting the probe placed on the probe holder.

The probe is thermally insulated in the low temperature container. The testing and manipulation device can be connected securely in a predetermined fashion to the test opening. This can be achieved using a flange-mounted connection. The area to be evacuated and thermally insulated is limited to the interior of the low temperature container; additional parts of the test and manipulation device do not have to be evacuated and cooled.

The probe to be investigated can be examined simultaneously from two sides. It is possible to manipulate the probe from one side, while testing the other side of the probe as radiation emitted from the probe is detected. "Manipulate" also means directing radiation via a test window onto the probe. The radiation emitted from the probe is analyzed using a second test window. More than two test openings can also be provided. The configuration of the tube pieces is naturally somewhat more complicated in the coinciding area of the probe holder.

The test opening and the probe holder are rigidly connected in a simple fashion. The thermal coupling of the tube piece to the radiation shield prevents the tube piece from becoming a "thermal bridge" between the test window and the cooling head. The probe is prevented from being shaded. Disturbing vibrations of the testing and manipulation device are kept at a distance.

A pulse tube cooler is preferably used as the mechanical cooling device because the pulse tube cooler generates fewer disturbing vibrations than do other mechanical cooling devices. The vibrations that are still present are rendered harmless by the novel arrangement of the test opening. The cooling device can also include a mixing cooler system or a 3He-4He mixing cooler system.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Reference will now be made in detail to some embodiments of the invention, examples of which are illustrated in the accompanying drawings.

Figure 1:
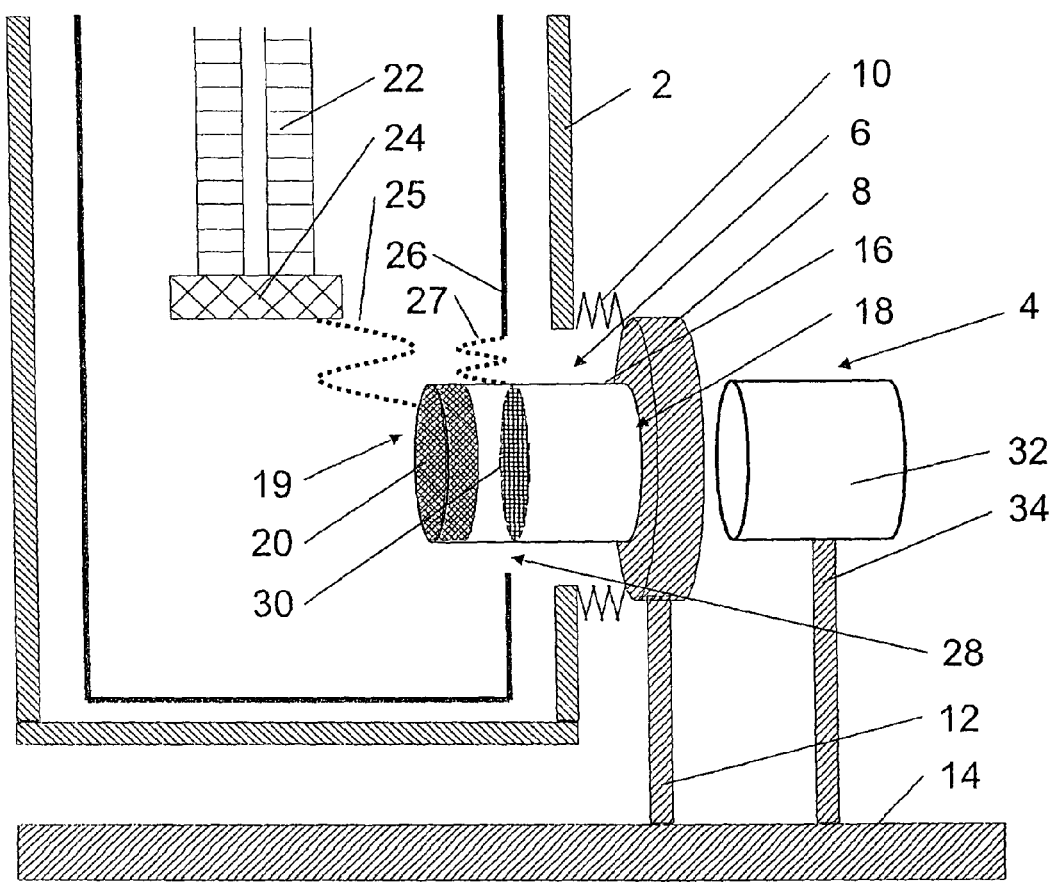
FIG. 1 is a schematic diagram of a first exemplary embodiment of the invention with a test opening.

FIG. 1 shows a first embodiment of the low temperature device that includes a low temperature container 2 with a closeable test opening 4. Low temperature container 2 is in the form of a Dewar container. The test opening 4 includes a recess 6 in low temperature container 2. In front of recess 6 is a test window 8 that includes a flange (not shown) that surrounds a disk that is permeable to radiation of a predetermined wavelength. A test window 8 is connected by a bellows 10 to low temperature container 2 and seals recess 6 from gas impingement. Test window 8 is rigidly supported on a low-vibration table 14 by a window support 12. A bilaterally open tube piece 16 has a first front side 18 and a second front side 19. The first front side 18 is securely connected to the inner side of test window 8. Tube piece 16 is made of a thermally insulating material, such as glass fiber reinforced plastic.

A probe holder 20 is situated at the second front side 19, which projects into the interior of low temperature container 2. A cooling device 22 projects into the interior of low temperature container 2. In one embodiment, cooling device 22 is a pulsed tube cooler. A cooling head 24 of cooling device 22 is thermally coupled (designed by reference numeral 25) to probe holder 20. The thermal coupling allows a probe (not shown) situated on probe holder 20 to be cooled to a desired operating temperature. Probe holder 20 with the probe is surrounded in the interior of low temperature container 2 by a radiation shield 26 in the form of a 70K shield. The 70K shield 26 includes an opening 28 that is penetrated by tube piece 16. Tube piece 16 is thermally coupled to 70K shield 26. This thermal coupling is designated by reference numeral 27.

A shield window 30 is provided in tube piece 16 and is situated at opening 28 of 70K shield 26. Shield window 30 is permeable to radiation from and to the probe.

Alternatively, the shield window can be omitted. An optical testing device 32 is placed on the outer side of test window 8. Optical testing device 32 is braced by a support 34 on the low-vibration table 14.

By having test window 8 of test opening 4 connected merely via bellows 10 to recess 6 in low temperature container 2, disturbing vibrations are not transferred to test window 8. If for example testing device 32 is rigidly connected to the outer side of test window 8, no mechanical oscillations are transferred to test device 32, or at least the oscillations are severely damped. By rigidly connecting probe holder 20 via straight tube piece 16 to the inner side of test window 8, probe holder 20 is mechanically decoupled from Dewar container 2 and pulsed tube cooler 22, even though probe holder 20 is situated in the interior of Dewar container 20. Test window 8 and probe holder 20, which are rigidly connected together, are braced by window support 12 on low vibration table 14. Low temperature container 2, such as a Dewar container, is not braced on low-vibration table 14.

Figure 2:
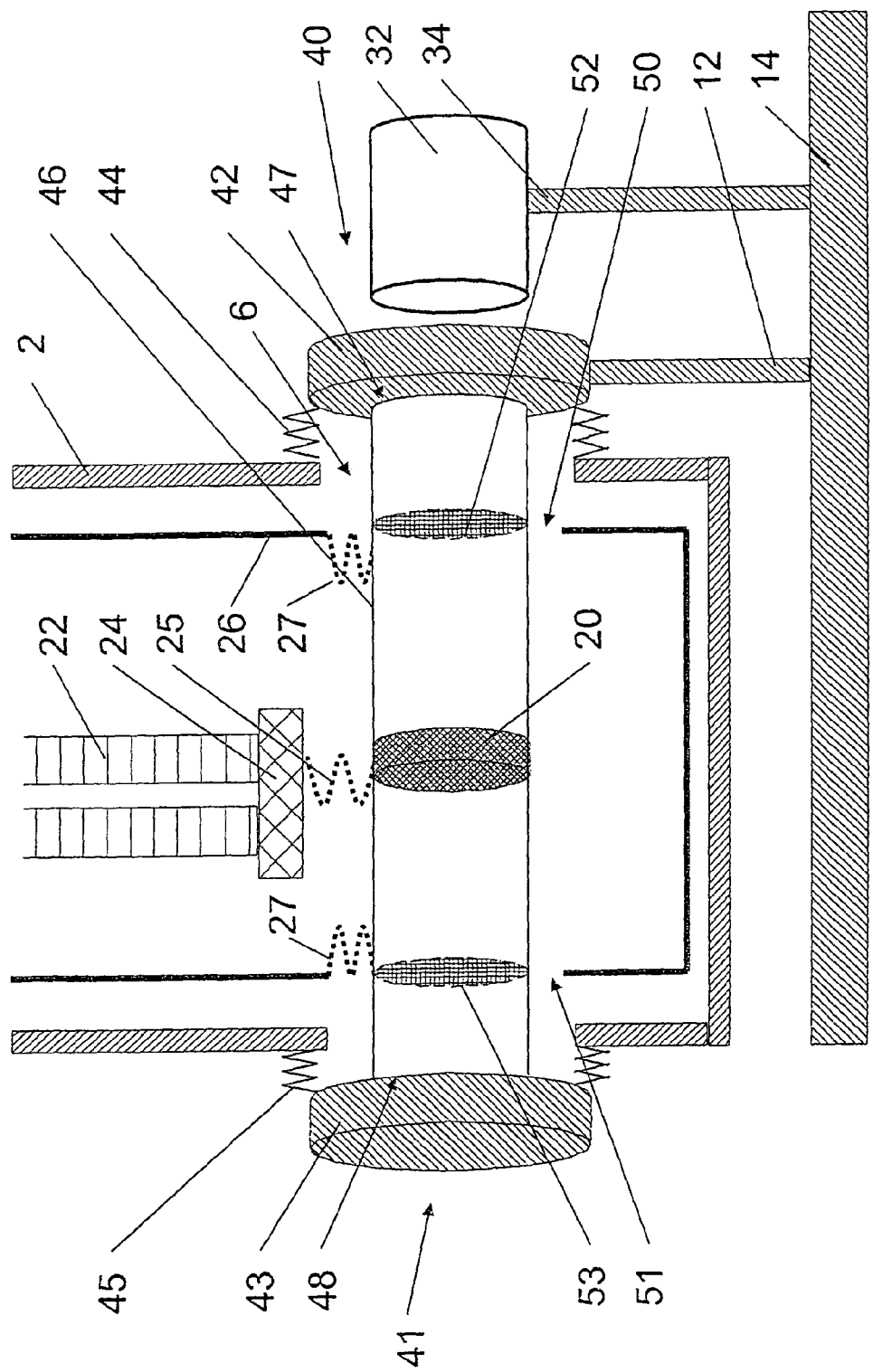
FIG. 2 is a schematic diagram of a second exemplary embodiment of the invention with two test openings.

FIG. 2 shows a second embodiment of the low temperature device. The embodiment of FIG. 2 differs from the embodiment of FIG. 1 in that the second embodiment has two instead of one test openings. Two test openings 40 and 41 are provided that are disposed opposite each other in low temperature container 2. The two test openings 40 and 41 are closed by a first test window 42 and a second test window 43. The two test windows 42 and 43 are connected to low temperature container 2 by a first bellows 44 and by a second bellows 45. A straight tube piece 46 extends between the two test windows 42 and 43 from a first front side 47 to a second front side 48. First front side 47 contacts the inner side of first test window 42, and second front side 48 contacts the inner side of second test window 43. The bilaterally open tube piece 46 is made of a thermally insulating material, such as plastic reinforced with graphite fiber. First test window 42 is braced to low-vibration table 14. Second test window 43 is rigidly connected to first test window 42 by tube piece 46. In this manner, supporting second test window 43 using an additional support directly to low vibration table 14 is not required. Nevertheless, second test window 43 can in analogous fashion be braced to first test window 42 by means of a support on low-vibration table 14.

Probe holder 20 is placed roughly in the middle of tube piece 46. Probe holder 20 is thermally coupled to a cooling head 24. This thermal coupling is indicated by reference numeral 25. The probe situated on probe holder 20 is visible through both test windows 40 and 41. As with the embodiment of FIG. 1, a 70K shield 26 is likewise provided for thermally insulating the area of the cooling head 24 and probe holder 20. The 70K shield 26 includes a first opening 50 and a second opening 51, which are penetrated by tube piece 46. A first shield window 52 and a second shield window 53 are provided in the two areas of tube piece 46 that protrude through first opening 50 and second opening 51 of 70K shield 26. First shield window 52 and second shield window 53 are permeable to radiation from and to the probe. In an alternative embodiment, the shield windows are omitted. The 70K shield 26 is thermally coupled to tube piece 46. This thermal coupling is designated by reference numeral 27. An optical testing device 32 that is braced to low-vibration table 14 is placed in front of first test window 40.

Those components that are used in measurements and investigations and that are sensitive to vibrations are braced to low-vibration table 14. These components are connected to the "vibrating" components of the low temperature device via flexible elements, such as bellows 44-45. In this manner, the vibrating components of the low temperature device are uncoupled from the testing and measurement device with regard to mechanical oscillations and vibrations.

Both of the embodiments described above include the 70K shield 26. However, additional radiation shields can also be provided to achieve other temperatures. The shield windows 30, 52 and 53 preferably are made of the same material as test windows 8, 42 and 43. Shield windows 52 and 53, as well as the two test windows 42 and 43, may include differing materials that are permeable to radiation of varying wavelengths.

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. A device comprising: a low temperature container; a probe holder disposed inside the low temperature container, wherein the probe holder is adapted to be attached to a probe that is to be investigated; a cooling device that is thermally coupled to the probe holder; a test window that is mechanically decoupled from the low temperature container; and a base, wherein the test window is mechanically coupled to the base outside the low temperature container and mechanically coupled to the probe holder via a tube piece such that mechanical oscillations of the low temperature container that are transferred to the test window are damped; wherein the tube piece has a first front side and a second front side, wherein the first front side is mechanically coupled to the test window, and wherein the second front side is mechanically coupled to the probe holder.

2. The device of claim 1, wherein the probe holder is mechanically decoupled from the cooling device.

3. The device of claim 2, wherein the cooling device includes a cooling head that is thermally coupled to the probe holder.

4. The device of claim 1, wherein the probe holder is mechanically coupled to the test window.

5. The device of claim 1, wherein the probe that is attached to the probe holder is visible through the test window.

6. The device of claim 1, wherein the low temperature container is a vacuum-sealed Dewar container.

7. The device of claim 1, wherein the low temperature container includes a radiation shield that provides thermal insulation to the probe that is attached to the probe holder.

8. The device of claim 1, wherein the test window includes a coupling device that couples the test window to an external testing and manipulation device.

9. The device of claim 1, wherein the test window is permeable to radiation of a predetermined wavelength such that radiation of the predetermined wavelength is directed to the probe that is attached to the probe holder.

10. The device of claim 1, wherein a test and manipulation device is disposed outside the low temperature container in front of the test window.

11. The device of claim 10, wherein the test and manipulation device is disposed on the base.

12. The device of claim 1, wherein the cooling device includes a mechanical cooling device.

13. The device of claim 12, wherein the cooling device includes a pulsed tube cooler.

14. The device of claim 12, wherein the pulsed tube cooler is a two-stage pulsed tube cooler.

15. The device of claim 1, wherein the test window is connected by a bellows to the low temperature container.

16. The device of claim 1, wherein a test opening is disposed in a recess in the low temperature container, and wherein the test opening includes the test window and the probe holder.

17. A device comprising: a low temperature container; a probe holder disposed inside the low temperature container; a test window that is mechanically decoupled from the low temperature container; the test window is mechanically coupled to a base outside the low temperature container and is mechanically coupled to the probe holder via a tube piece such that mechanical oscillations of the low temperature container that are transferred to the test window are damped; wherein the tube piece has a first front side and a second front side, wherein the first front side is mechanically coupled to the test window, and wherein the second front side is mechanically coupled to the probe holder; and a cooling head of a cooling device, wherein the cooling head is thermally coupled to the probe holder.

18. The device of claim 17, wherein the test window is connected by a bellows to the low temperature container.

19. The device of claim 17, wherein a test opening is disposed in a recess in the low temperature container, and wherein the test opening includes the test window and the probe holder.

20. A device comprising: a low temperature container; a probe holder adapted to be attached to a probe that is to be investigated; a cooling device disposed inside the low temperature container, wherein the cooling device is thermally coupled to the probe holder; and a test window that is mechanically coupled to a base outside the low temperature container and that is mechanically coupled to the probe holder via a tube piece and that is mechanically decoupled from the low temperature container such that mechanical oscillations of the low temperature container that are transferred to the test window are damped: wherein the tube piece has a first front side and a second front side, wherein the first front side is mechanically coupled to the test window, and wherein the second front side is mechanically coupled to the probe holder.

21. The device of claim 20, wherein an optical testing device is disposed on the base.

22. The device of claim 20, wherein the test window is connected by a bellows to the low temperature container.

23. The device of claim 1, wherein the tube piece is made of a material taken from the group consisting of: glass fiber reinforced plastic and plastic reinforced with graphite fiber.

* * * * *